United States Patent [19]

Moody

[11] Patent Number: 4,951,316
[45] Date of Patent: Aug. 28, 1990

[54] SUN VISOR WITH EYESHIELD AND METHOD THEREFOR

[76] Inventor: Monty L. Moody, 2720 N. 68th St., Suite 5-499, Scottsdale, Ariz. 85257

[21] Appl. No.: 390,414

[22] Filed: Aug. 7, 1989

[51] Int. Cl.⁵ .......................... A42B 1/20; A42B 1/24
[52] U.S. Cl. ............................................. 2/10; 2/12; 351/155
[58] Field of Search .................. 2/10, 12, 199, 453, 2/185 R, 9; 351/155, 158, 118

[56] References Cited

U.S. PATENT DOCUMENTS

| | | | |
|---|---|---|---|
| 2,619,641 | 12/1952 | Vaca | 2/10 |
| 3,649,107 | 3/1972 | Hoffmaster et al. | 351/118 |
| 4,541,125 | 9/1985 | Phillips | 2/453 X |
| 4,592,096 | 6/1986 | Glasheen | 2/453 X |
| 4,815,838 | 3/1989 | Liautaud | 2/12 X |
| 4,819,274 | 4/1989 | Day | 2/10 |

*Primary Examiner*—Peter Nerbun
*Attorney, Agent, or Firm*—Harry M. Weiss

[57] ABSTRACT

An improved sun visor with eyeshield in which the eyeshield can be positioned, in a positive and secure manner, both up and down and at incremental distances from the wearer's eyes so as to allow the wearer to keep his/her face and eyes shaded as the direction of direct and reflected sunlight changes during the course of a day.

1 Claim, 1 Drawing Sheet

U.S. Patent
Aug. 28, 1990
4,951,316
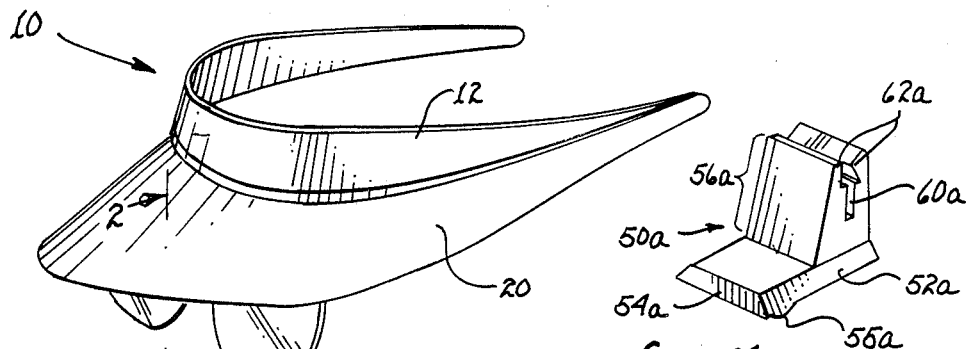
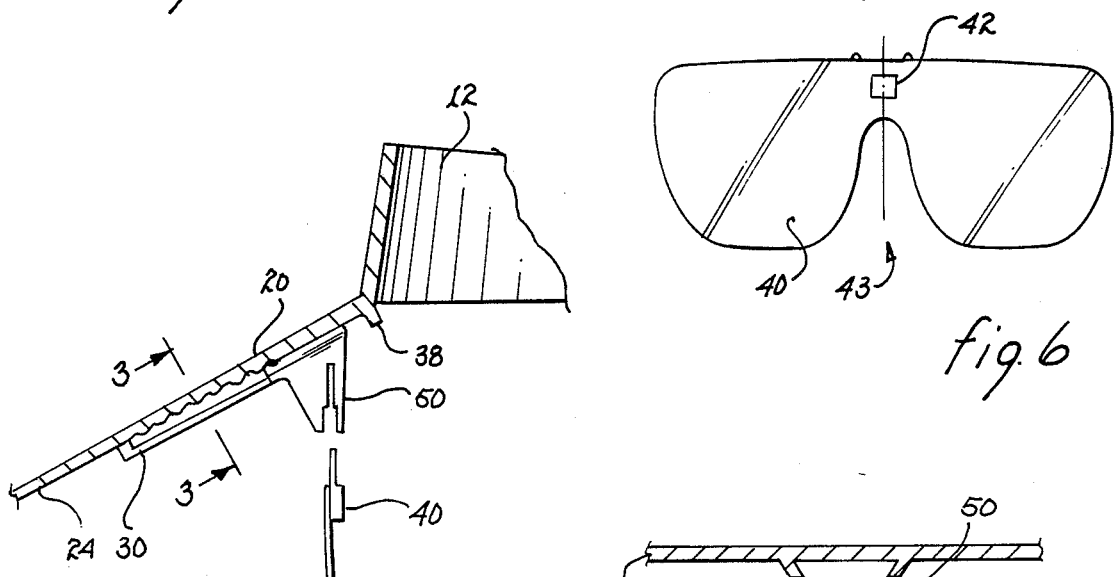
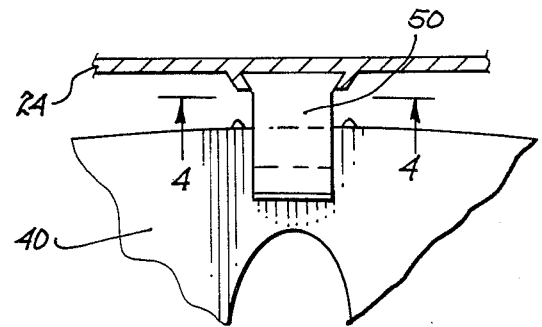
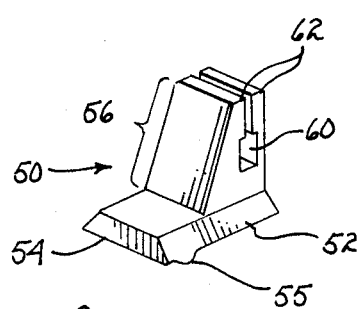
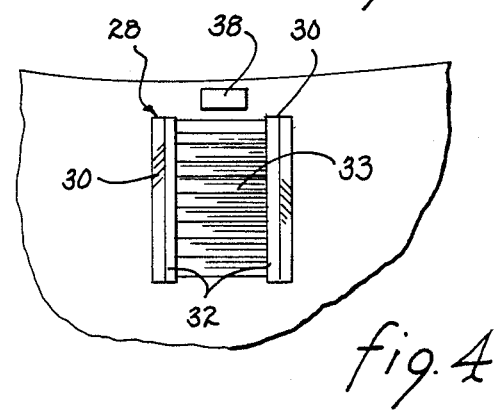

SUN VISOR WITH EYESHIELD AND METHOD THEREFOR

BACKGROUND OF THE INVENTION

1. Field of Invention

This invention relates generally to devices and methods therefor used to shade a person's forehead, eyes and face from the sun and, more particularly, to an improved sun visor and method therefor having an eyeshield whose position can be adjusted to keep the face and eyes shaded as the direction of direct and reflected sunlight changes, during the course of a day.

2. Description of the Prior Art

In the past, a number of devices have been proposed, to protect a person's face from the sun, wind, particulate matter or the bright light emitted during welding. These devices combined a cap type structure with an eyeshield that could be positioned either up or down. Examples of these kinds of devices are disclosed in U.S. Pat. Nos. 2,654,089, 2,648,091, 2,467,448 and 1,709,765. An advance on this art, which can be found in U.S. Pat. Nos. 3,837,005 and 2,619,641, was an eyeshield that not only could be positioned up and down but could also be positioned at variable distances from the wearer's eyes. U.S. Pat. No. 4,819,274 discloses a visor type cap with a detachable eyeshield, which can be positioned both up or down and at various distances from the wearer's eyes. However, the detachable eyeshield in this prior art reference has a tendency to slide or slip from its position requiring the user to be constantly readjusting the position of the eyeshield.

Thus, there is a need for an improved sun visor with a removable eyeshield that can shade the forehead, face and eyes of the wearer from direct and indirect sunlight, in which the eyeshield is positively and securely attached in its various adjustable positions and thus is less susceptible to slippage.

SUMMARY OF THE INVENTION

An object of the present invention is to provide an improved sun visor with eyeshield and method therefor in which the eyeshield can be adjusted, in a positive and secure manner, to keep the face and eyes of the wearer shaded as the direction of direct and indirect sunlight changes, during the course of a day.

Another object of the present invention is to provide a slippage free eyeshield device and method therefor for attachment to a sun visor that will allow the wearer to pivot the eyeshield up and down and move the eyeshield preset incremental distances from his/hers eyes.

These and other objects, features and advantages of the present invention, as well as details of the preferred embodiment thereof, will be more fully understood from the following description and drawing.

BRIEF DESCRIPTION OF THE DRAWING

FIG. 1 is a perspective view of the preferred embodiment of the present invention;

FIG. 2 is a cross sectional view taken along line 2—2 in FIG. 1, with the eyeshield removed;

FIG. 3 is a partial cross sectional view taken along line 3—3 in FIG. 2 showing the coupling of the eyeshield to the bottom of the sun visor;

FIG. 4 is a bottom view of the sun visor showing the track to which the coupling can be attached;

FIG. 5 is a perspective view of the coupling also shown in FIGS. 1,2 and 3;

FIG. 6 is a front view of the eyeshield also shown in FIGS. 1,2 and 3;

FIG. 7 is a perspective view of an alternative embodiment of the coupling shown in FIG. 5.

DESCRIPTION OF THE PREFERRED EMBODIMENT

Referring to the drawings, FIG. 1, shows the improved sun visor with eyeshield generally designated by reference number 10 having a forehead protecting and/or attaching member 12, a visor 20 and an eyeshield 40. The forehead protecting member 12 and the visor 20 are preferably integrally formed from plastic, with the visor 20 projecting over the eyes and face of the wearer.

FIG. 4 shows a track member 28 on bottom side 24 of the visor 20. The track member 28 is integral with the visor 20 and preferably consists of two edge members 30 parallel to each other and running longitudinally along the bottom side 24 creating a dovetailed channel 32. Within the channel 32 are a series of grooves 33 that are parallel to each other and run between the edge members 30. A stop member 38 is positioned right behind the rear side of the channel 32 (see also FIG. 2). FIG. 6 shows the eyeshield 40 having the general shape of conventional sun glasses with an integral slot 42 preferably positioned along the centerline 43 of the eyeshield 40. The eyeshield 40 is integrally made from any desired filtering material, such as colored plastic or glass.

FIG. 5 shows coupling 50 which is preferably integrally molded from plastic and used to couple the eyeshield 40 to the visor 20. The coupling 50 has a dovetailed top portion 52 sized and shaped to slide into the dovetailed channel 32. Along edge 54 of the top portion 52 is detent 55 shaped and sized to mate with and engage each of the grooves 33. Base portion 56 of the coupling 50 preferably contains a snap lock type member 58 having a single chamber 60 and two prongs 62. A minimum spacing is generally maintained between the prongs 62 by the natural rigidity of the material from which the coupling 50 is made.

FIG. 7 shows an alternative embodiment 50a of the coupling 50. Elements common to both couplings will be designated by like numerals with the numerals designating elements in the alternative embodiment 50a having the subscript a.

With respect to the use and operation of the improved sun visor with eyeshield 10, (see FIGS. 2 and 3), the wearer selects any suitable eyeshield 40. The eyeshield 40 is then slid into the snap lock type member 58. As the edge of the eyeshield 40 comes into contact with the prongs 62, the prongs 62 are parted. Once the edge of eyeshield 40 slides beyond the prongs 62 and entered the chamber 60, the prongs encounter the slot 42. The prongs 62 are no longer held apart and return to their original spacing firmly holding the eyeshield 40 in place while still permitting the eyeshield 40 to be rotated.

The coupling 50, with eyeshield 40 attached, is then slid into the front of the track member 28. As both the channel 32 and the top portion 52 are dovetailed, the two edge members 30 prevent the coupling 50 from moving in any direction other than forward or backward along the track member 28. Unrestricted movement forward or backward along the track member 28 is prevented by the detent 55 which can engage any of the grooves 33. By applying a slight torque at the base 56 of the coupling 50, the detent 55 is raised away from and does not engage the grooves 33. The coupling 50 is only then free to move forward or backward along the channel 32. When the desired distance from the wearer's eyes is reached, the wearer releases the torque at the base 56 of the coupling 50 and the detent 55 is brought into contact with and engages one of the grooves 33 locking the eyeshield 40 firmly in place. At this point the wearer can flip the eyeshield 40 either up or down as desired. This procedure can be repeated as often as the wearer desires. The stop 38 prevents the wearer from moving the eyeshield 40 too close to his/her eyes. To remove the eyeshield 40 or to adjust the distance, the wearer applies a slight torque to the base 56 of the coupling 50, as previously described, raising the detent 55 away from the grooves 33. The eyeshield 40 is now free to be moved to a different distance from the wearer's eyes or to be slid forward, away from the wearer's eyes, until it slides entirely out of the channel 32, at the bottom portion thereof.

While the invention has been particularly shown and described with reference to a preferred embodiment thereof, it will be understood by those skilled in the art that changes in form and detail may be made therein without departing form the spirit and the scope of the invention.

I claim:

1. An improved sun visor with eyeshield, comprising in combination:

a sun visor having an integral dovetailed channel with a plurality of grooves enclosed therein, said dovetailed channel having an opening at one end;

an eyeshield having a slot; and means, for coupling said eyeshield to said visor, having a dovetailed, top portion having a rigid detent means, disposed along an edge of said top portion, for positively engaging said grooves and a bottom portion having snap lock means comprising two prongs, separated by a distance slightly less than the thickness of said eyeshield, for snap locking onto said slot of said eyeshield.

* * * * *